July 2, 1946. P. J. SCHMIDT Plant Pat. 706

BUDDLEIA PLANT

Filed Nov. 9, 1945

WITNESS

Addison J. Avery

INVENTOR:

Paul J. Schmidt.

ATTORNEY:

John H. Leonard.

Patented July 2, 1946

Plant Pat. 706

UNITED STATES PATENT OFFICE

706

BUDDLEIA PLANT

Paul J. Schmidt, Youngstown, Ohio, assignor to The Wayside Gardens Company, Mentor, Ohio, a corporation of Ohio Application November 9, 1945, Serial No. 627,654

1 Claim. (Cl. 47—60)

This invention relates to a new variety of Buddleia plant and particularly to a purple Buddleia having certain distinguishing characteristics as hereinafter set forth.

The present Buddleia was produced by me by crossing Buddleia Eleanor as the seed or female parent with Buddleia Flaming Violet, which is disclosed in United States Plant Patent No. 519, as the pollen or male parent. The seeds produced as a result of this cross were planted and the present plant was selected from among those produced from the seed and was first asexually reproduced by root cuttings.

*The drawing*

*The plant generally*

Figures 1, 2, 3, 4:
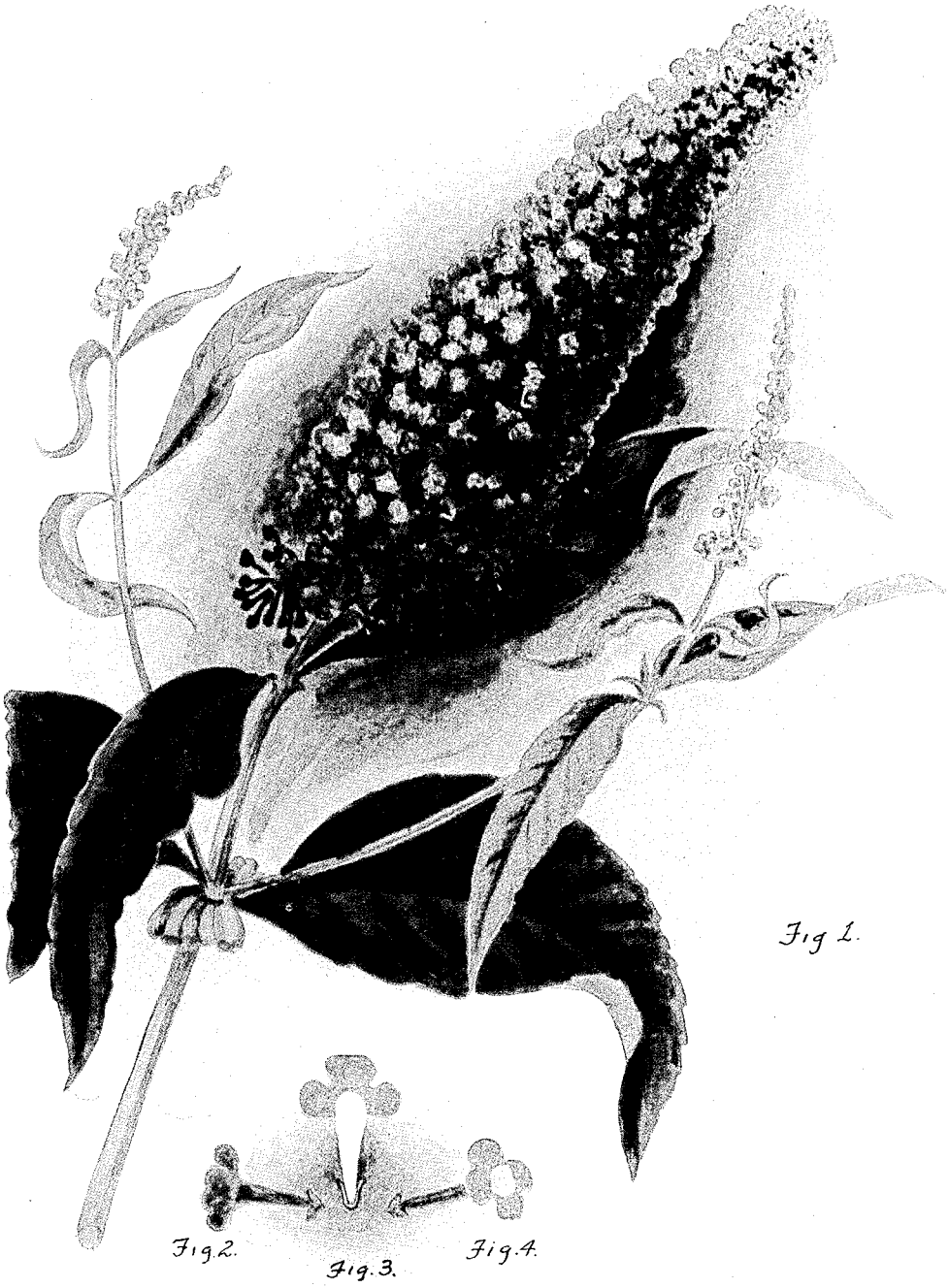
Fig. 1 is a reduced side elevation of the terminal portion of one of the main lateral branches of the plant with the terminal inflorescence of the branch in full bloom thereon and with sublateral branches bearing inflorescences in various stages of growth, illustrating its compact composition and blunted tip and the detail of the florets and their arrangement in the inflorescence.
Fig. 2 is an enlarged essentially side elevation of one of the florets viewed from slightly rearwardly of the floret.
Fig. 3 is an enlarged longitudinal sectional view of one of the florets showing the color of the interior of the funnel.
Fig. 4 is an essentially side elevation of one of the florets viewed from a position slightly forwardly of the floret.

The plant has openly branched roots which, for this type of plant, are large, very strong, and of robust growth. The plant is deep rooted with a lateral root spread somewhat greater than that of the upper portion of the plant as is usual for Buddleias. The resistance of the roots to disease is exceptional. The roots withstand both wetness and drouth very well. They are very hardy with exceptional winter resistance when protected and with good resistance when unprotected, having withstood temperatures as low as four degrees below zero in Ohio when unprotected.

The plant grows well in almost any good soil wherein winter drainage is good. In general the exposed portion of the plant is bushy, reaching an average height of from four to five feet. It is regular in contour and very vigorous in growth. The exposed plant has exceptional resistance to low temperature when protected and good resistance when unprotected. Its disease resistance is exceptional and its resistance to drouth and wetness is good. The plant prefers the full sun with an exposure other than north and well drained soil varying from clay loam to sandy loam. In shade it does not produce good flowers.

The main stalks are upright, straight and stiff and very well branched. It is one of the strongest growing Buddleias now in existence. The color of the stalks is uniform for similar portions, the darker portions being bluish green comparable to Maerz and Paul Plate 39–A–4, the brownish portions being comparable to Maerz and Paul Plate 8–H–3 and the light portions of the stalks being comparable to Maerz and Paul Plate 20–G–1 and with a slight purplish cast adjacent to the inflorescence. The main stalks vary in length from four to five feet, are smooth textured and grow in groups from the roots. They are oppositely branched. The foliage is very compact, the leaves being oppositely arranged and abundant. On their top surfaces the leaves are a green comparable to Maerz and Paul Plate 23–J–1 through 23–L–7, and on their under faces have a silvery cast comparable to Maerz and Paul Plate 20–A–1 through 20–A–3. The leaves are much larger and longer than is usual for Buddleias and are very wide. On a full grown plant the leaves, near the flower head, are about three and one half inches in length and, about two feet above the ground, are six inches in length. The width of the leaves near the flower head is from two to two and one half inches, while the width of those nearer the ground is as much as three inches. They are comparatively thick with smooth upper surfaces and fuzzy under surfaces and their persistence on the plant is excellent.

The best flowers are produced in a full sun with an exposure other than north and in a well drained moist neutral soil, with rich loam, sandy loam, clay or clay loam soils being preferred. Though the plant will grow well in poorer and sandy soils the flower heads which are produced are not as large or as well developed.

The blooming period extends from July through October, usually until the first frost during which period the plant blooms continuously. The inflorescences are straight and very large, with an average diameter of three to four inches and a length from ten to twelve inches for the terminal inflorescences of the main stalks. The inflorescences of the laterals are generally slightly smaller. The terminal inflorescences of the main stalks generally are of uniform diameter for about two thirds of their length and then taper gradually for the remaining third to a blunt rounded tip which is about one half the diameter of the uniform diameter portion. In the drawing the portion of uniform diameter has been shortened slightly relative to the tapering portion so as to better disclose the gradual taper to the blunt tip and at the same time the compact arrangement of the individual florets.

The inflorescences are borne on the stalks and branches without drooping, their axes being continuations, without curvature or break, of the axes of their supporting stalks or branches. The average plant bears from fifty to sixty flower heads which remain in good condition on the blooming plant for about a week. They have a very good permanence as cut flowers, the inflorescences being in good condition for as long as three or four days after cutting. The individual florets of a given inflorescence bloom almost simultaneously and produce a very compact well filled out and rounded flower head which is very fragrant. The individual florets are much longer than usual and appear to average about 50% greater in length than the florets of other Buddleias.

The geenral tone of the inflorescence is a purple or violet ranging from a color comparable to Maerz and Paul Plate 42–K–6 through wild aster comparable to Maerz and Paul Plate 44–L–9. The single florets have petals of purple or violet color the inner portion of the petal being Belladonna comparable to Maerz and Paul Plate 44–J–7 with outer borders comparable to Maerz and Paul Plate 42–K–6. The back of the petals is a slightly duller tone comparable to Maerz and Paul Plate 44–K–7. The tube portions on the outer surface are a purple violet comparable to Maerz and Paul Plate 45–K–8. The throat and inside of the funnel of individual florets is of an orange color comparable to Maerz and Paul Plates 9–C–11 through 9–L–11. The color varies somewhat depending upon soil, weather and light conditions.

The plant is characterized particularly in that it has larger leaves and stronger stems than is customarily found in Buddleias. It is a very quick and sturdy growing plant. The golden eye of individual florets is different from that of other varieties and the florets open almost all at the same time. The inflorescence as a whole is large and is shaped differently from that customarily found in Buddleia in that it has a broad base and full rounded tip. The color also is exceptional and different. Another characterizing feature is that the inflorescences are borne on the stiff, straight stalk and stiff, lateral branches with the axes of the inflorescences forming a continuation of the axes of their associated main stalks or branches without break or curvature so that the inflorescences are supported generally in upright position and without drooping of the inflorescences as a whole or of any portion thereof.

I claim:

A new and distinct variety of Buddleia plant herein shown and described and characterized particularly by large leaves; its rapid and sturdy growth; the golden eye or interior of the funnel and color of the petals; the concurrent opening of almost all the florets of a head; the straight, stiff, sturdy stalks supporting the flower heads in coaxial relation without break or curvature; and the large size, well rounded contour, and rounded blunt tip, of the inflorescence as a whole.

PAUL J. SCHMIDT.